(12) United States Patent
Burgi et al.

(10) Patent No.: US 7,976,548 B2
(45) Date of Patent: Jul. 12, 2011

(54) SURGICAL TOOL HOLDER FOR FACILITATED STERILIZATION

(75) Inventors: Jonas Burgi, Moutier (CH); André Lechot, Orvin (CH)

(73) Assignee: Greatbatch Medical S.A., Orvin (CH)

( * ) Notice: Subject to any disclaimer, the term of this patent is extended or adjusted under 35 U.S.C. 154(b) by 587 days.

(21) Appl. No.: 11/686,490

(22) Filed: Mar. 15, 2007

(65) Prior Publication Data

US 2007/0167952 A1 Jul. 19, 2007

Related U.S. Application Data

(63) Continuation-in-part of application No. PCT/IB2005/003720, filed on Dec. 30, 2005, now abandoned.

(60) Provisional application No. 60/783,900, filed on Mar. 20, 2006, provisional application No. 60/710,845, filed on Aug. 24, 2005.

(51) Int. Cl.
*A61B 17/58* (2006.01)
*A61B 17/60* (2006.01)
*A61F 2/00* (2006.01)
*G05G 1/00* (2008.01)

(52) U.S. Cl. ............................... 606/99; 74/544
(58) Field of Classification Search ............ 606/99; 74/544

See application file for complete search history.

(56) References Cited

U.S. PATENT DOCUMENTS

| | | | |
|---|---|---|---|
| 1,942,422 A | 1/1934 | Hanna | |
| 4,305,394 A | 12/1981 | Bertuch, Jr. | |
| 4,475,549 A | 10/1984 | Oh | |
| 4,587,964 A | 5/1986 | Walker et al. | |
| 4,632,111 A | 12/1986 | Roche | |
| 4,716,894 A | 1/1988 | Lazzeri et al. | |
| 4,765,328 A | 8/1988 | Keller et al. | |
| 4,919,679 A | 4/1990 | Averill et al. | |
| 5,037,424 A | 8/1991 | Aboczsky | |
| 5,190,549 A | 3/1993 | Miller et al. | |
| 5,324,293 A | 6/1994 | Rehmann | |
| 5,364,403 A | 11/1994 | Petersen et al. | |
| 5,417,696 A | 5/1995 | Kashuba et al. | |
| 5,443,471 A | 8/1995 | Swajger | |
| 5,540,697 A * | 7/1996 | Rehmann et al. ............ | 606/91 |
| 5,584,837 A | 12/1996 | Petersen | |
| 5,658,294 A | 8/1997 | Sederholm | |
| 5,683,399 A | 11/1997 | Jones | |
| 5,720,750 A | 2/1998 | Koller et al. | |
| 6,063,124 A | 5/2000 | Amstutz | |
| 6,205,884 B1 * | 3/2001 | Foley et al. ................... | 74/544 |

(Continued)

FOREIGN PATENT DOCUMENTS

EP 0470912 A2 2/1992

(Continued)

*Primary Examiner* — Thomas C. Barrett
*Assistant Examiner* — David Bates
(74) *Attorney, Agent, or Firm* — Michael F. Scalise

(57) ABSTRACT

A surgical tool holder aids a surgeon in controlling the use of a tool during, for example, preparation of a femoral cavity for reception of hip joint prosthesis. The holder has a housing that encloses a mechanism having, at a far end, a tool-engaging interface, and at the opposite end, a handle which facilitates manipulation of the tool during use in preparing a bone site by the surgeon. The holder enables easy orientation of the tool attached to its end, which is important because control of the tool is critical in order to accurately prepare a recess for reception and installation of a prosthesis.

24 Claims, 15 Drawing Sheets

U.S. PATENT DOCUMENTS

| | | |
|---|---|---|
| 6,451,058 B2 | 9/2002 | Tuke et al. |
| 6,626,913 B1 * | 9/2003 | McKinnon et al. ............. 606/99 |
| 2003/0050645 A1 | 3/2003 | Parker et al. |
| 2003/0229356 A1 | 12/2003 | Dye |
| 2005/0038443 A1 | 2/2005 | Hedley et al. |
| 2005/0222572 A1 | 10/2005 | Chana |
| 2005/0228395 A1 | 10/2005 | Auxepaules et al. |
| 2007/0093897 A1 * | 4/2007 | Gerbec et al. ............. 623/17.11 |
| 2007/0156155 A1 | 7/2007 | Parker |
| 2007/0167952 A1 | 7/2007 | Burgi et al. |
| 2007/0293869 A1 | 12/2007 | Conte et al. |
| 2008/0021481 A1 | 1/2008 | Burgi |

FOREIGN PATENT DOCUMENTS

| | | |
|---|---|---|
| WO | WO 01/06964 | 2/2001 |
| WO | 2005044153 A1 | 5/2005 |

* cited by examiner

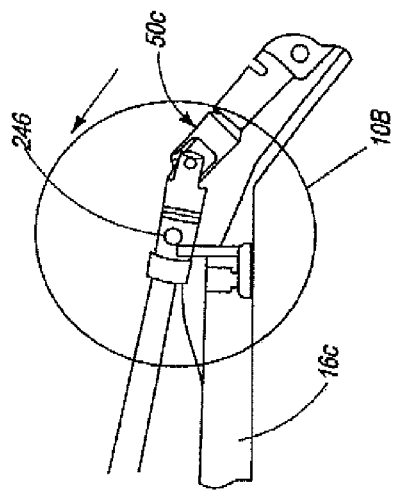
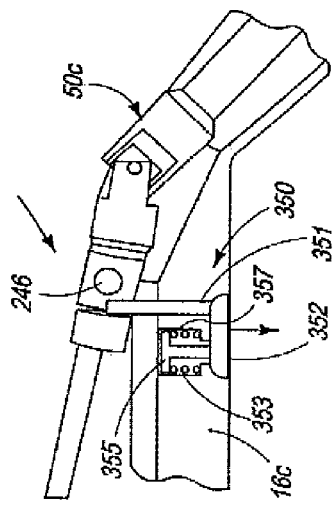
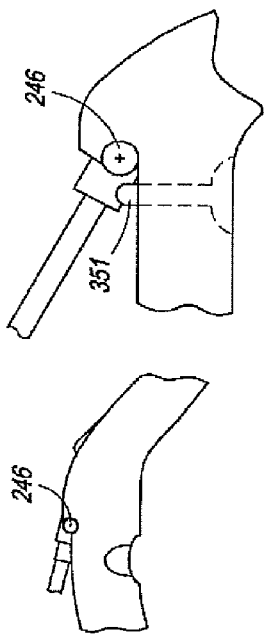
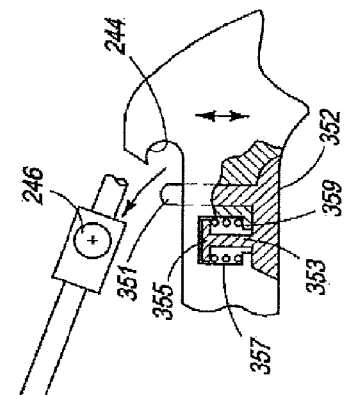
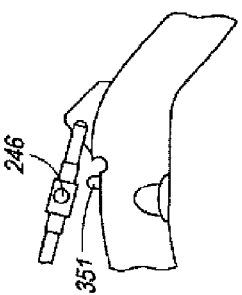
FIG. 10A
FIG. 10B
FIG. 10C
FIG. 10D

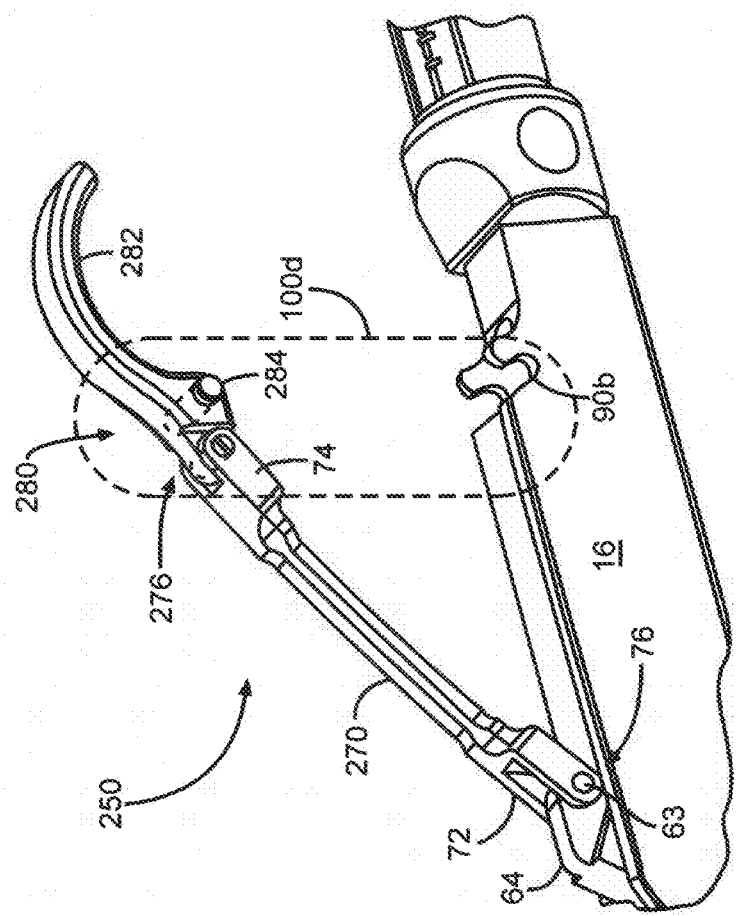

SURGICAL TOOL HOLDER FOR FACILITATED STERILIZATION

CROSS-REFERENCE TO RELATED APPLICATIONS

The present application claims priority to previously filed U.S. Patent Application Ser. No. 60/783,900, filed Mar. 20, 2006 and is a continuation-in-part of PCT Patent Application Serial Number PCT/IB2005/003720 (now abandoned), filed Dec. 30, 2005, both of which are incorporated by reference herein, the PCT claiming benefit under 35 U.S.C. §119(e) of U.S. Provisional Application No. 60/710,845, filed Aug. 24, 2005.

FIELD OF THE INVENTION

This invention relates to surgical tools for aiding in the installation of orthopedic prostheses in patients. More particularly, the present invention relates to easily sterilizable holders for use with a surgical tool in preparing a bone site, and for use in installing a prosthesis in the bone.

BACKGROUND OF THE INVENTION

Complicated mechanical devices have crevices and recesses that are difficult, if not almost impossible to clean with ease without disassembly into separate component parts. Devices that are not properly cleaned and sterilized increase the risk of disease transfer from patient to patient. This is especially true following the emergence of certain "prions" that are not killed by normal hospital sterilization.

Further, in surgical procedures in which access to the treatment site is limited, it is difficult to use current solutions without subjecting the patient to repeated abrasion and tissue trauma when inserting and extracting surgical instruments.

Additionally, the insertion of a prosthetic implant is often problematic, and the orientation of the implant in a properly prepared recess is often critical to minimize recovery time of the patient. Still further, once the appropriate position of the tool is selected, it is often difficult to ensure that the position does not change upon insertion of the assembly through the incision.

It would be beneficial, therefore, to have an orthopedic tool holder that is easily adjustable, disassemblable, and cleanable. Additionally, it would be beneficial if the tool holder can be partially disassembled for cleaning without the need to completely separate any of the component parts completely from the device as a whole. Further, it would be beneficial to have a holder that enables the surgeon to better maneuver and position a tool head to facilitate preparing a bone site to receive a prosthetic implant in a particular angular orientation.

SUMMARY OF THE INVENTION

A surgical tool holder aids a surgeon in controlling the use of a tool during surgery, for example, during preparation of a femoral cavity for reception of hip joint prosthesis. The present invention is such a surgical tool holder, but adapted to facilitate sterilization. The adaptation is a "break-away" feature that additionally provides a tool holder that allows partial disassembly to facilitate sterilization, while remaining loosely intact to prevent the separation of component parts from the device as a whole.

The present surgical holder has a housing which encloses a break-away, surgical tool engagement mechanism. At one end, the present tool holder has a tool or prosthesis engaging interface. At the opposite end, the holder has a handle or grip which facilitates manipulation of the holder and positioning of an attached tool during use. The holder enables easy orientation of the surgical tool or other device attached to its interface. This is important, because control is critical in order to accurately prepare a bone site for receiving a prosthesis, and for installing a prosthesis in the site.

An objective of the present invention is to be easily cleaned and sterilized. This is accomplished by the holder including a tool head engagement mechanism that easily breaks-away (unfolds) from the rest of the device, but remains attached as a module. This object of the invention eliminates the need to disassemble the tool holder into separated pieces, and minimises the risk that pieces could be lost. The disassembled/unfolded condition allows access to all surfaces to be cleaned and sterilized. Cleaning and sterilization is further facilitated by the holder having a reduced number of small radius internal corners, crevices and small gaps, and by the absence of blind holes. Another object of the invention is to provide a tool holder which enables an attached tool or prosthesis to be firmly locked against rotation or rocking.

BRIEF DESCRIPTION OF THE DRAWINGS

FIGS. 10A to 10D are partial cross-sectional side views of an embodiment of the present surgical tool holder illustrating a further alternative releasable locking mechanism for positively retaining the tool holder drive chain linkage within the housing.

FIG. 13A is a perspective view of a surgical tool holder of the present invention illustrating an alternative configuration of the tool holder linkage assembly including a cam-pin engagement lever locking feature.

DETAILED DESCRIPTION OF THE PREFERRED EMBODIMENT(S)

Figure 1A:
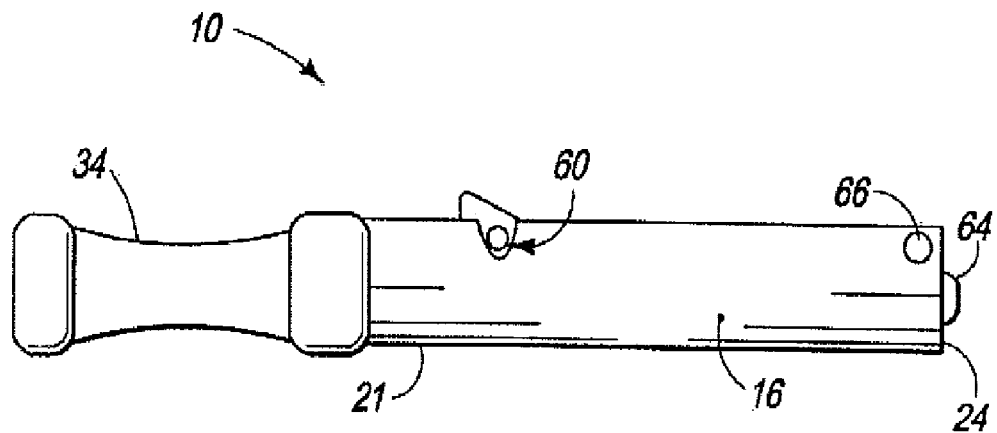
FIGS. 1A and 1B are side view schematics illustrating the present surgical tool holder in an assembled/ready-to-use condition, and in a disassembled/unfolded condition for cleaning and/or sterilization, respectively.

The present invention is a surgical tool holder configured for facilitated cleaning and sterilization. Various surgical/orthopedic tool heads useful for surgical procedures can be mounted on the tool holder. The present surgical tool holder includes a tool holder linkage having an interface for attaching a tool head to the holder. The tool holder linkage is partially removable from the body of the surgical tool holder to facilitate cleaning and sterilization of the device as a whole. The tool holder linkage intentionally is only partially removable from the body of the handle to prevent its component parts from being separated from the device as a whole, for example during cleaning, handling or storage, and so as to avoid the parts subsequently becoming lost or misplaced. Various surgical/orthopedic tool heads useful for surgical procedures can be mounted on the tool holder.

An objective of the present invention is to be easily cleaned and sterilized. This is accomplished by the holder including a tool head engagement linkage that easily breaks-away (unfolds) from the rest of the device, but remains attached as a module. This object of the invention eliminates the need to completely disassemble the tool holder into separated pieces, and minimizes the risk that pieces could be lost. The disassembled/unfolded condition is intended to allow access to all surfaces to be cleaned and sterilized. Cleaning and sterilization is further facilitated by the holder having a reduced number of small radius internal corners, crevices and small gaps, and by the absence of blind holes.

Referring now to the drawings, the details of preferred embodiments of the present invention are graphically and schematically illustrated. Like elements in the drawings are represented by like numbers, and any similar elements are represented by like numbers with a different lower case letter suffix.

Figure 1B:
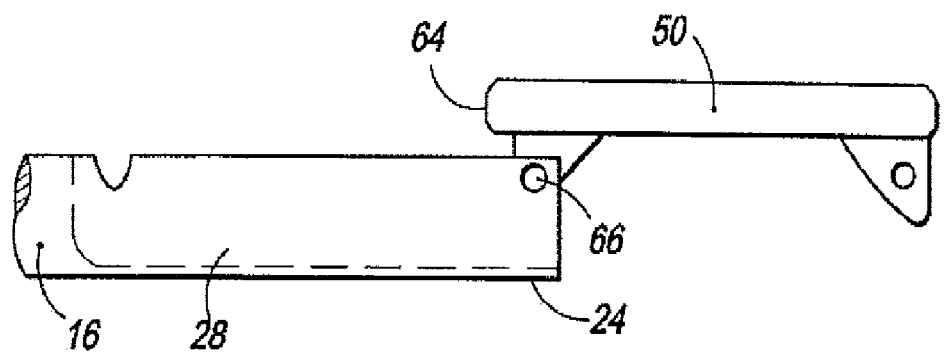

The present invention is a break-away surgical tool holder 10 as generally exemplified in FIGS. 1A and 1B. As such, the present surgical tool handle 10 includes all of the materials composition limitations expected of such a tool for surgical use and subject to sterilization procedures. Additionally, the present surgical tool holder 10 includes a tethered tool holder linkage assembly that has new structural features and functional aspects that distinguish it from prior surgical tool holders. More specifically, the tool holder 10 has a break-away tool holder linkage assembly 50 that allows the tool holder linkage 50, which during use is normally retained in the housing 16 of the holder 10 in a linkage chamber 28 (see FIG. 1B), to be released and swung or folded out of the housing 16 for cleaning. A feature of the tool holder 10 is that when disassembled to this folded out condition, cleaning and sterilization of the holder 10 is facilitated, without any of the component parts of the holder 10 having to be separated from the device as a whole. As noted above, this feature prevents the loss of any parts of the holder during cleaning/sterilization or during use in a surgical procedure.

Figure 2A:
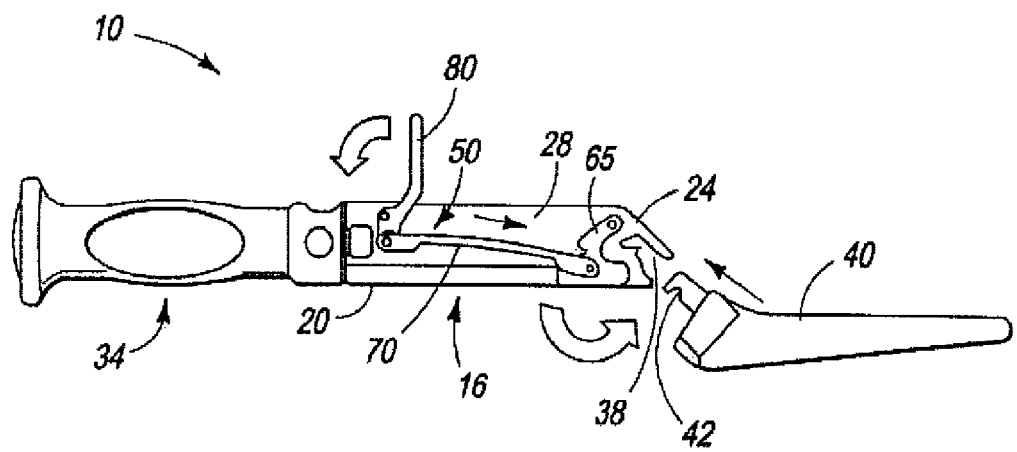
FIG. 2A is a partial cross-sectional side view of a surgical tool holder of the present invention illustrating the tool holder mechanism in an "open" configuration, i.e., ready to receive a surgical or orthopedic tool for attachment to the handle.
Figure 2B:
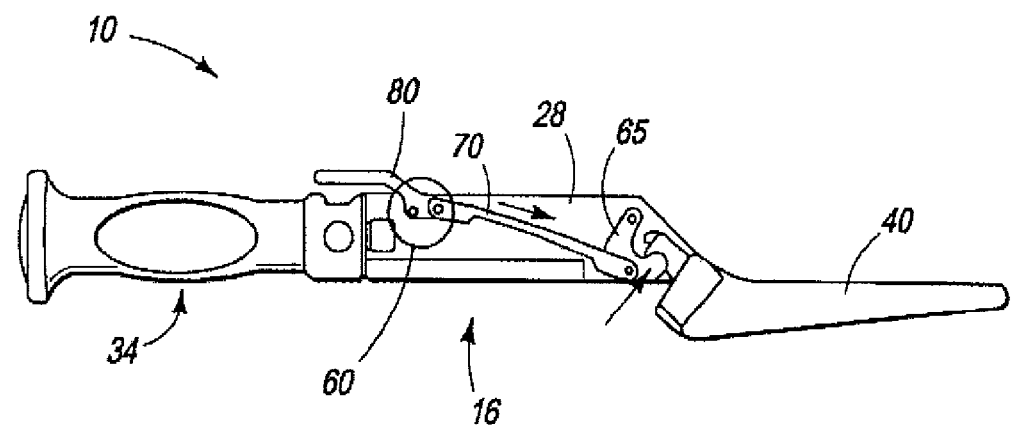
FIG. 2B is a partial cross-sectional side view of a surgical tool holder of the present invention illustrating the tool holder mechanism in a "closed" configuration and a surgical tool (a broach) attached to the handle.

In a preferred embodiment illustrated in FIGS. 2A and 2B, the body of the surgical tool holder 10 includes an elongated housing 16, having a grip end 20, a tool end 24, and a linkage chamber 28. The tool holder linkage 50 is received within the linkage chamber 28. A hand grip 34 is attached to the housing 16 at the grip end 20. A tool insertion port 38 is disposed at the tool end 24 of the housing 16 for receiving a surgical tool head 40, such as a surgical rasp in the embodiment illustrated. A tool holder linkage 50 is received within the linkage chamber 28. The linkage 50 allows a tool head 40 to be attached to or removed from the tool end 24 of the surgical tool holder 10. The tool holder linkage 50 is tethered at its tool holder end 54 (see FIG. 3A) to the interior of the linkage chamber 28 as described below. The other end or the linkage retainer end 56 (see FIG. 3A) of the linkage 50 communicates with a linkage lock mechanism 60 to hold the tool holder linkage 50 within the linkage chamber 28 and to secure the attachment of the tool head 40 to the housing 16. The linkage assembly 50, in combination with the tool interface 38, allows a tool head 40 to be attached to or removed from the tool end 24 of the surgical tool holder 10.

Figure 3A:
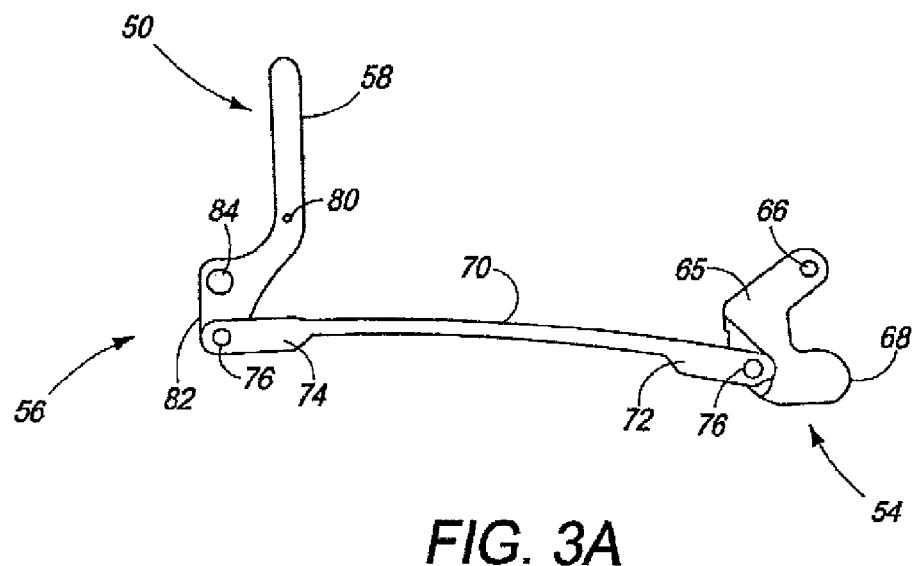
FIG. 3A is a side view of a tool holder linkage of the present invention.
Figure 4:
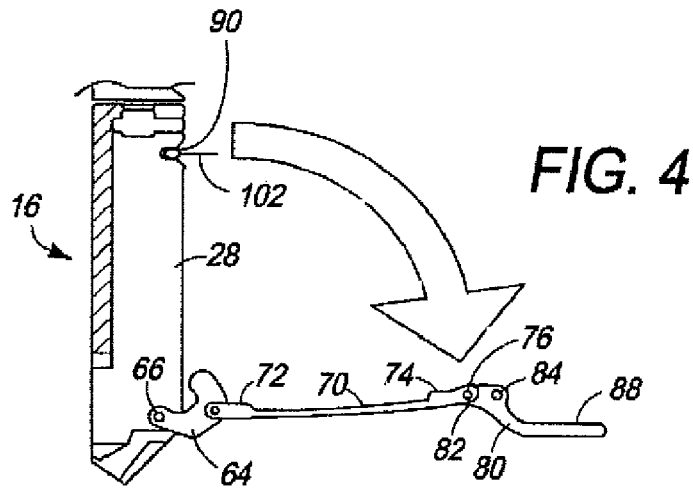
FIG. 4 is a partial cross-sectional side view of the housing of the present tool holder showing the tethered relationship of the tool holder linkage to the housing.

The tool linkage 50 in FIG. 2 is further illustrated in FIG. 3A. The linkage 50 has a tool holder end 54 and a linkage retainer end 56. A tool interface 64, comprising a locking pawl 65 and the tool port 38 in this embodiment, is disposed at the tool holder end 54 of the linkage 50. The locking pawl 65 swivels about a pivot pin 66 received in an opening 69 in the pawl 65. The pivot pin 66 has a length that is sufficient to tether the entire tool holder linkage assembly 50 to the interior of the linkage chamber 28, allowing the rest of the linkage 50 to be swung out of the chamber 28 to facilitate cleaning/sterilization without any of the component parts of the device having to be separated from the device as a whole. See FIG. 4.

Figure 3B:
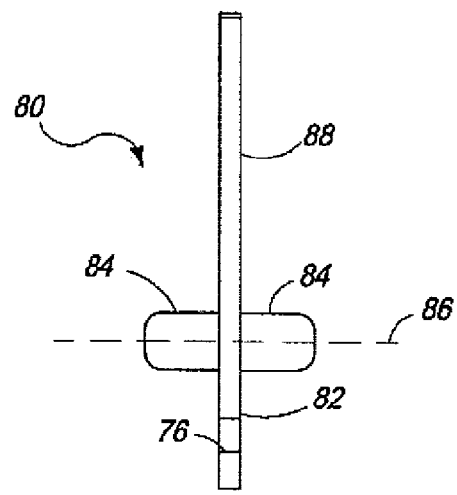
FIG. 3B is an end-on view of an engagement lever of the tool holder linkage of FIG. 3A.

As shown in FIGS. 3A and 3B, the locking pawl 65 is in driven communication with the drive (distal) end 72 of a torsion connecting rod 70 via a mechanical movement coupling device 76. In the embodiment illustrated in FIGS. 2A to 3A and 4, the connecting rod 70 is a "torsion" connecting rod as explained below. Alternatively, non-torsion connecting rods may be practiced in the invention as exemplified below. The drive end 72 of the torsion rod 70 is connected to the locking pawl 65 by a pawl pin 63 and causes the locking pawl 65 to swivel on pivot pin 66 in response to movement of the torsion rod 70. The torsion connecting rod 70 has a driven (proximal) end 74 in communication with the lever follower arm 82 of an engagement lever 80 at the linkage retainer end 56 of the tool holder linkage 50.

In the preferred embodiment illustrated in FIG. 3B, the engagement lever 80 has a pair of opposed lever pins 84 centered on an engagement lever axis of rotation 86 about which the engagement lever 80 is pivotable. The elongated housing 16 includes a pair of catch recesses 90 (FIG. 4), each catch recess 90 disposed to pivotably receive a lever pin 84 of the pair of lever pins to mount the engagement lever 80 to the housing 16. The engagement lever 80 is pivotable when the lever pins 84 are received in the catch recesses 90, so that moving the lever handle 88 of the engagement lever 80 brings the follower arm 82 to bear against the drive end 74 of the torsion connecting rod 70. In the preferred embodiment shown, the mechanical movement coupling 76 used at either end of the torsion rod 70 is a simple pivot-pin swivel connector, such as is known to the ordinary skilled artisan in view of the illustrations. Other coupling devices are known to and selectable by one of skill in the art for practice of the present invention as well.

Figure 5A:
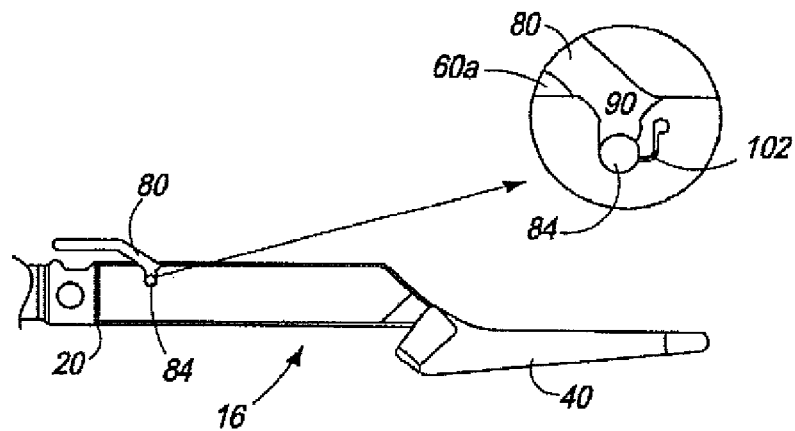
FIGS. 5A, 5B and 5C are side views of a portion of the housing illustrating alternative releasable locking mechanisms for positively retaining the tool holder linkage within the housing.
Figure 5B:
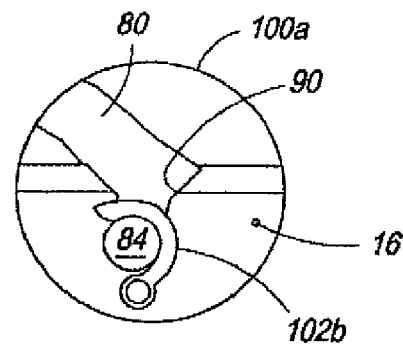
Figure 5C:
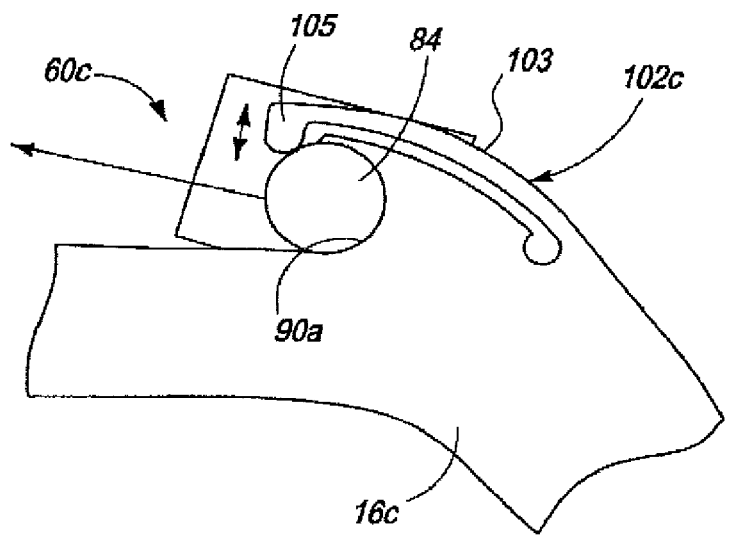

As shown in FIG. 5A, a linkage lock mechanism 60a is disposed proximate the grip end 20 of the housing 16. The linkage lock mechanism 60a engages the engagement lever 80 to retain the tool holder linkage 50 in the linkage chamber 28. In a preferred embodiment of the linkage lock mechanism 60a illustrated in FIG. 5A, one of the lever pins 84 of the engagement lever 80 is engaged to retain the tool holder linkage 50 (FIG. 3A) in the linkage chamber 28. In the illustrated embodiment, a detent bias 102 associated with a catch recess 90 normally bears against a lever pin 84 received in the catch recess 90 to hold the lever pin 84 in place and retain the holder linkage 50 in the linkage chamber 28. In the embodiment illustrated, the detent bias 102 bearing against the lever pin 84 is integral to and inseparable from the housing 16. Other locking mechanisms are available as well. For example, in FIG. 5B, the linkage locking mechanism has a detent bias hook 102b bearing against the lever pin 84 to hold the lever pin 84 received in the catch recess 90. The detent bias hook 102b is not integral, but is attached to and separable from the housing 16. In this embodiment the detent bias 102b is a spring hook on a swivel pin. In another example illustrated in FIG. 5C, the linkage locking mechanism 60c has a detent bias 102c bearing against the lever pin 84 to hold it received in the catch recess 90a. The detent bias 102c had a flexible finger 103 extending from (and integral to) the housing 16c and crossing over the lever pin 84. A blocking head portion 105 of the detent bias finger 102c provided the force to hold the lever pin 84 against the catch recess 90a. Again, the detent bias 102c bearing against the lever pin 84 is integral to and inseparable from the housing 16c. However, other detent bias devices are known to and selectable by one of ordinary skill in the art for practice in the present invention.

FIGS. 1A to 4 illustrate use of this embodiment of the holder 10. In FIG. 2A, the linkage assembly 50 is received, but not locked, in the linkage chamber 28. A tool head 40, such as a surgical rasp, is introduced into the tool port 38. Pushing down on the handle 88 of the engagement lever 80 causes the torsion connecting rod 70 to move as indicated. This movement is communicated to the locking pawl 65 causing its locking face 68 (see FIG. 3A) to engage a detent 42 in the tool head 40 to secure the tool 40 to the handle 10. The disposition of components of the linkage 50, upon the action of engaging the lever 80, torques the connecting rod 70 over its length causing a constant force to be exerted at both of its ends 72 and 74 when the linkage 50 is configured in its closed and locked configuration. This force holds the locking pawl 65 engaged with the tool detent notch 42, and acts to keep the engagement lever 80 toggled in the closed position. For cleaning and sterilization, the engagement lever 80 is manually released from the linkage lock mechanism 60 and the tool holder linkage 50 swiveled from the linkage chamber 28 to make it accessible for cleaning.

Figure 6:
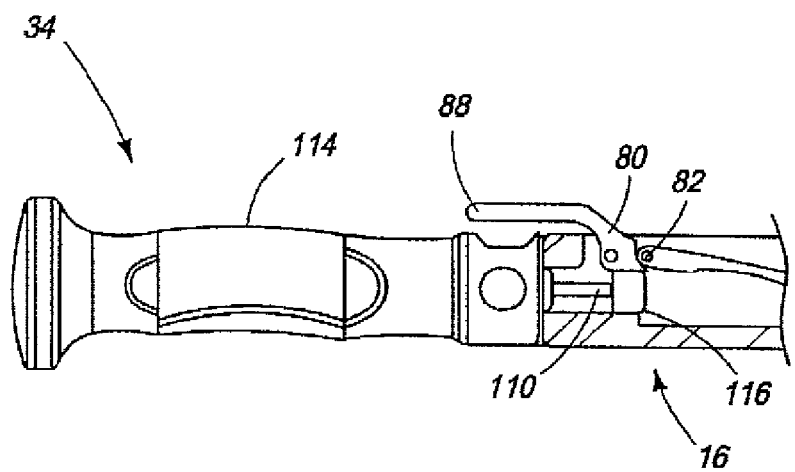
FIG. 6 is a partial cross-sectional side view of a surgical tool holder of the present invention illustrating an alternative configuration of the tool holder mechanism including an engagement lever locking feature.

Optionally, in addition to the linkage lock mechanism 60 in this embodiment, a lever lock 110 can be practiced in the present surgical tool holder 10, as depicted in FIG. 6, according to some embodiments. A lever lock 110 is a device for further preventing the lever handle 88 of the tool holder linkage 50 from being inadvertently operated from the closed configuration. The lever lock 110 comprises the setting of an obstruction 116 closely adjacent the follower arm 82 of the engagement lever 80 to prevent an inadvertent force on the handle lever 88 from causing the engagement lever 80 to rotate. In the embodiment shown, the rotation of a section 114 of the grip 34 causes extension of the obstruction block 116 from its retracted position (see FIGS. 1A and 1B) to its locking position. A change in the texture of the hand grip 34 is useful for indicating the configuration of the lever lock 110—retracted or extended. Mechanisms for accomplishing the movement of the block 116 by rotation of sections of the hand grip 34 relative to each other are known in the art, and are selectable by the ordinary skill artisan and accomplished in the present invention.

Figure 7A:
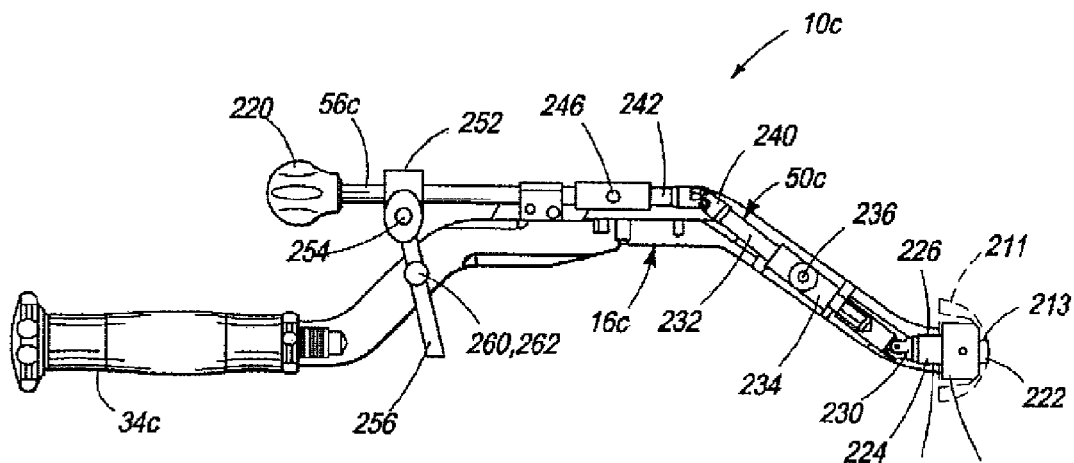
FIG. 7A is a partial cross-sectional side view through the housing of the tool holder in an alternative embodiment of the present invention.
Figure 7B:
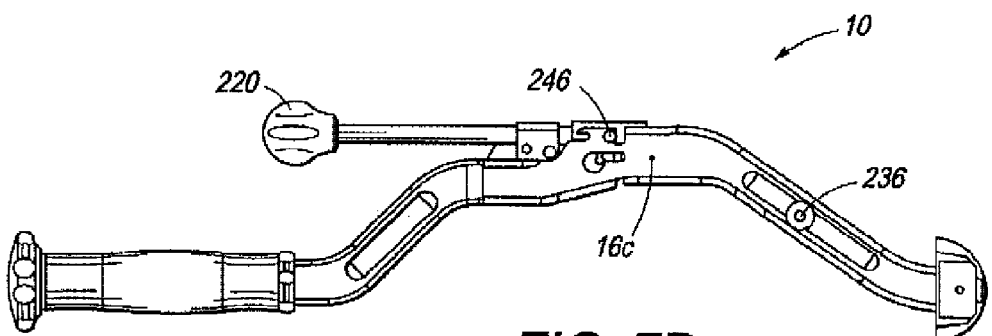
FIG. 7B is a side view of an embodiment of the present surgical tool holder showing the tool holder linkage assembly retained in the housing.

The tool holder linkage assembly 50 of the present invention can structurally and functionally be more than just a device for attaching a tool head to the holder 10. In another preferred embodiment illustrated in FIG. 7A and subsequent drawings, the break-away tool holder linkage assembly 50 comprised a tool head drive chain 50c disposed within the linkage chamber. In use, the tool head drive chain 50c is retained in large part within the housing 16c. An attachment 211, such as a surgical tool, a surgical appliance or a prosthetic element, is installable to the tool end 54c of the drive chain 50c at a tool interface 213. At the retainer end 56c of the drive chain 50c a handle 220 is fixed to the pivoting lever 242 of the drive chain 50c. Rotation of the handle 220 by a user is transmitted via the drive chain 50c and imparted to the attachment 211 (see FIG. 5A). In the embodiment illustrated, the holder 10c is configured to aid a surgeon in controlling the installation of an acetabular cup prosthesis. The housing 16c is C-shaped, as shown, in order to minimize the invasiveness of the surgery by better clearing anatomical structures and tissue. The drive chain 50c is thus not in the same plane as the handle 220.

The interface 213 is cut on a boss 222 on a cylindrical piston 224 which slides in an axial hole 226 in the housing head 264 of the housing 16c. The interface 213 is preferably threaded. In the preferred embodiment illustrated, the head 264 is a polymeric impactor head molded over the tool end 54c of the housing 16c. A molded polymeric head is useful to absorb impact stresses incurred during use of the present tool holder 10 as a surgical impactor. The housing head 264 is also selected so as to have good frictional characteristics as well. Nevertheless, a metal, non-molded housing head 264 may also be used with satisfactory results. The piston 224 is connected by way of a first U-joint 230 to a lever 232, which slides in a pivoting sleeve 234 fixed to the housing 16c via a pivot 236. The lever 232 is connected via a second U-joint 240 to the second pivoting lever 242, which is fixed to pivot in a catch 244 (see FIG. 9A) on a pivot pin 246. The catch 244 is essentially a seat or detent cut into the housing 16c, against which the pivot pin 246 of the lever 242 is captured when a slide 250 (see FIGS. 8B and 9A) is slid over the pivot pin 246 when it is engaged against the catch 244.

The lever 242 has a slidable sleeve 252, through which it passes. The lever 242 has a trunnion 254 to which a rod 256 is pivotally attached. The rod 256 passes through a one-way catch 260, a type of linkage lock mechanism in the housing 16c. The one-way catch 260 prevents the rod 256 from sliding out of the housing 16c, unless a release (not shown) is operated. The one-way catch 260 can be a captured split wedge sleeve 262 having an inner diameter that just matches the outer diameter of the rod 256, and which is captured in a recess having a matching conical surface that surrounds the sleeve so as to allow the rod 256 to slide into the housing 16c, but to prevent the rod from sliding out, the release is operated. The release could be a lever for merely lifting the sleeve 262 out of engagement with the conical surface so as to unlock and to permit the rod 256 to back out of the housing 16c. However, this is just an example, and any number of alternative one-way lock devices may be used, the selection of which being within the skill of a person of ordinary skill in this field.

Figure 7C:
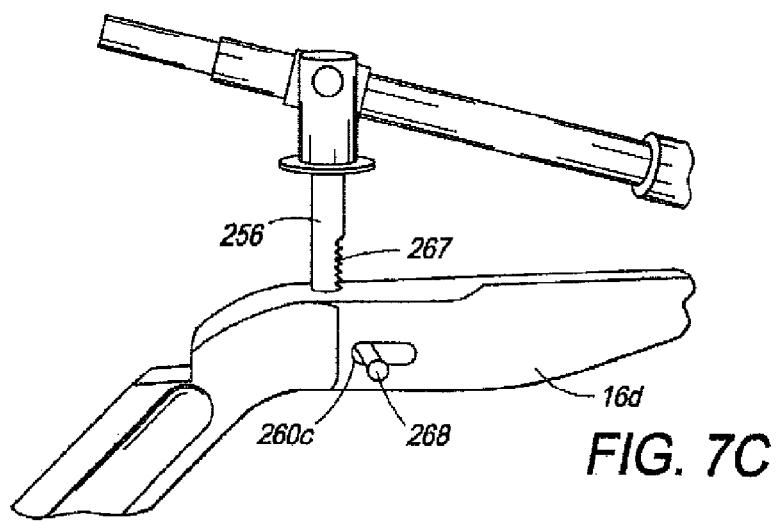
FIG. 7C is a perspective view of the present tool holder illustrating an example of a one-way catch mechanism.

For example, FIG. 7C illustrates an alternative embodiment of a one-way catch mechanism 260c. In this embodiment, the rod 256 passes through a one-way catch 260c in the housing 16d. The one-way catch 260c has an inner recess that matches the outer diameter of the rod 256. The inner recess has a ratchet pawl (not shown) that locks against one-way ratchet teeth 267 so as to allow the rod 256 to slide into the housing 16d, but to prevent the rod 256 from sliding out, unless a release lever 268 is operated. In the example illustrated, release is accomplished by operating the lever 268 to merely pull the pawl away from the teeth 267 to permit the rod 256 to back out of the housing 16d.

Figure 8A:
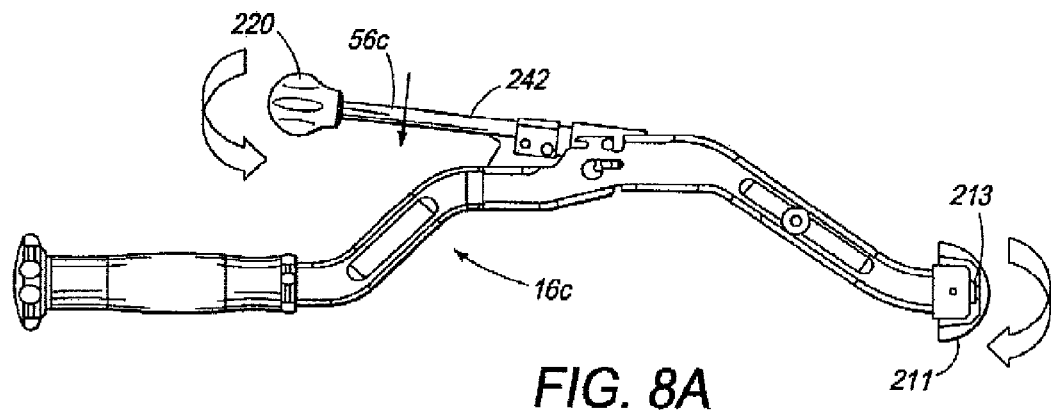
FIG. 8A is side view of an embodiment of the present surgical tool holder illustrating the operational feature of the tool holder linkage assembly and its relationship to an attached tool.
Figure 8B:
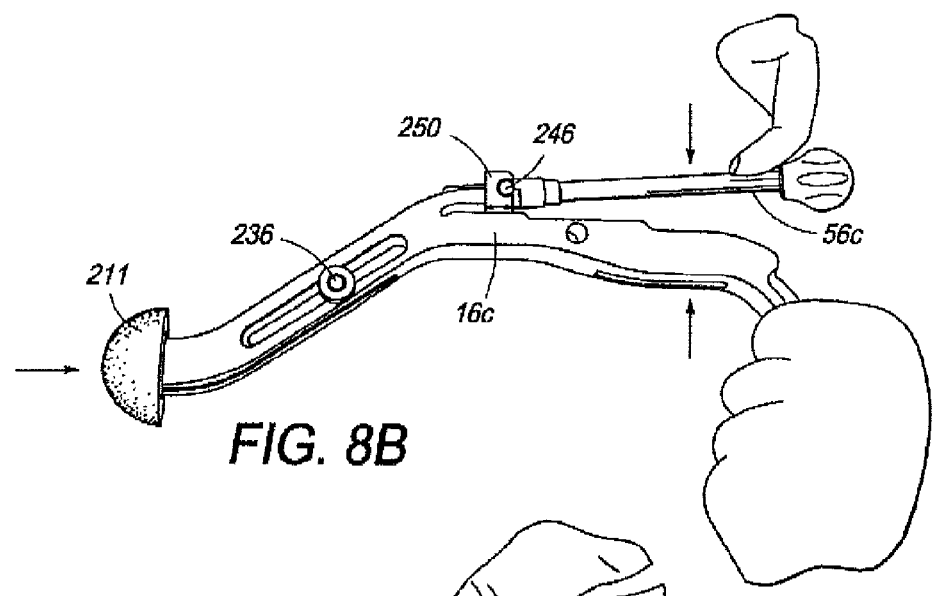
FIG. 8B is a perspective view of the present surgical tool holder illustrating the use of the one way locking mechanism to lock an installed attachment against the holder's housing head.
Figure 9A:
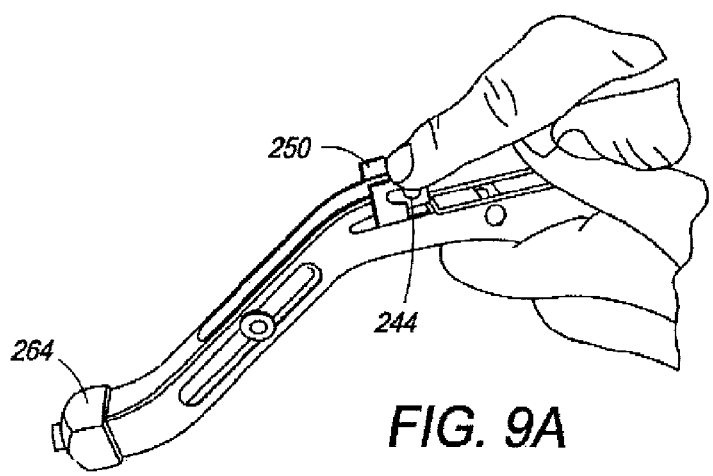
FIGS. 9A to 9D are perspective views of an embodiment of the present tool holder showing various stages of disassembly for cleaning and reassembly for use.
Figure 9B:
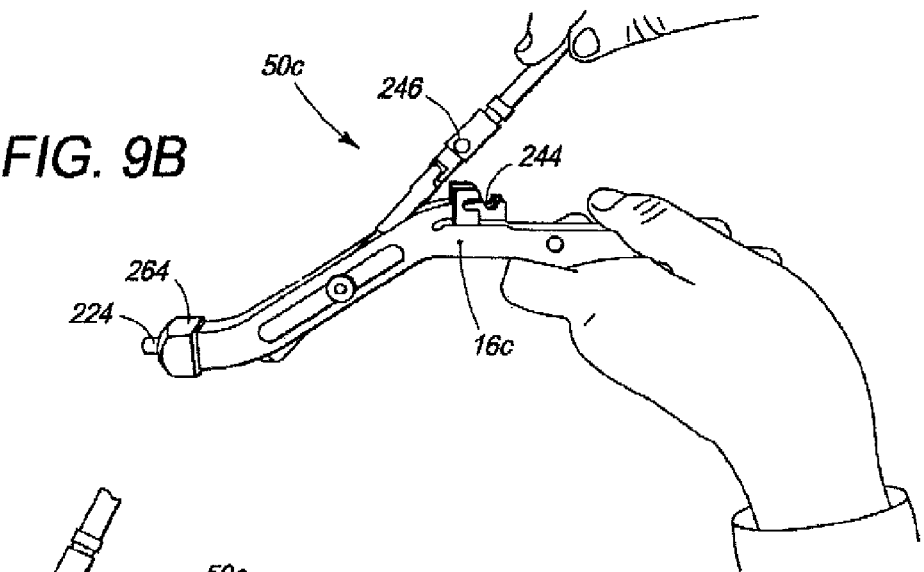
Figure 9C:
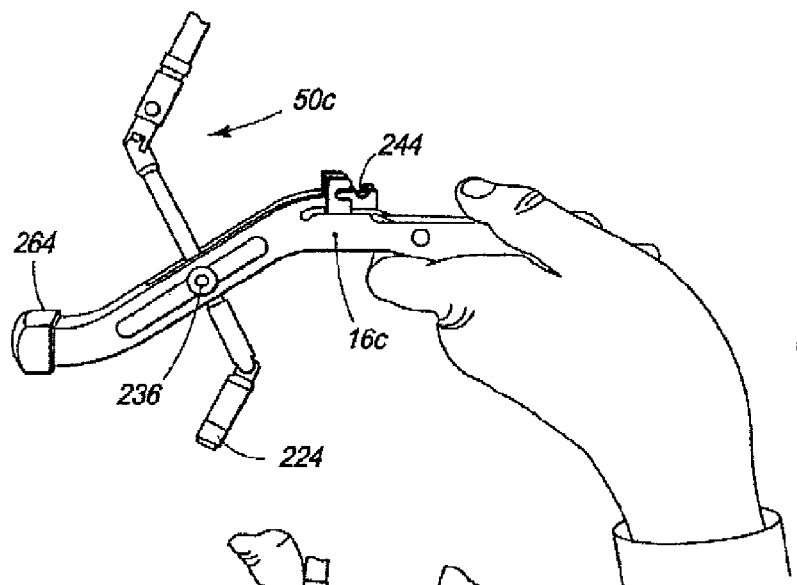
Figure 9D:
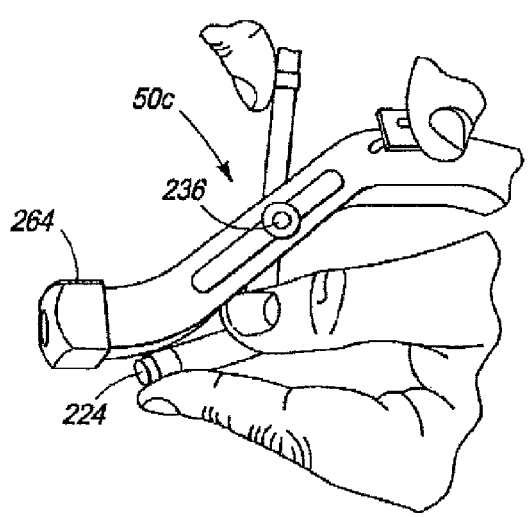

Referring now to FIGS. 8A and 8B, in operation the interface (preferably threaded) of the piston is engaged with the prosthesis 211. When the operator rotates the handle 220 about the axis of the pivoting lever 242, this rotates the drive train 50c, which in turn rotates the piston. Rotation of the piston can be used to attach the interface 213 to an attachment 211 to impart rotational force to an attachment 211 already engaged in the interface 213, or to orient the attachment 211 in a desired position. This last feature is particularly useful when the attachment is a prosthesis being installed in a bone site.

As illustrated in FIG. 8B, when the retainer end 56c of the drive lever 242 is urged downwardly toward the housing 16c, movement is transmitted through the drive train 50c to draw the piston 24 into the housing 12, and thus to cause the attachment 211 to be drawn against the housing head 264 of the housing 16c. This contact serves to create a normal force between the attachment 211 and the head 264 as to prevent rotation of the attachment 211 relative to the housing 16c. The operator may use the one-way locking mechanism 262 to lock the lever 242 in a position so as to lock the attachment 211 against the housing head 264. One of the benefits of this feature is that the operator can pre-set and lock the position of the attachment 211 prior to engaging it with the bone site. Note that this feature is particularly beneficial when the attachment 211 is a prosthetic device. This is because a prosthesis often has pre-drilled holes, which must be properly positioned prior to fastening through these at the installation site.

The "easily cleaned" feature of the present invention enables access to all surfaces, so that they can be cleaned, i.e., parts covering other parts can be moved to expose all surfaces for cleaning and sterilization. Also, the present invention is practiced with a reduction in number of small radius internal corners, crevices and small gaps, and the absence of blind holes. Referring now to FIGS. 9A to 9D, in the embodiment shown, the device 10 is disassembled for cleaning by simply sliding the slide 250 back to release the pivot 246 and then folding the drive train 50c out of the housing 16c. However, the drive chain 50c remains tethered to the housing 16c by the pivot pin 236. As the drive train 50c is swung out of the housing 16c, the piston 224 is drawn out of the hole 226 in the housing 16c. To reassemble holder after cleaning, the piston 224 is reinserted into the hole 226 and the drive train 50c is swung back into housing 16c, with the one-way locking mechanism entering its receiver and the pivot 246 again entering into the catch 244. The slide 250 is then slid over the pivot 246 and the present surgical tool holder 10 is again ready for use.

Referring now to FIGS. 10A-10D, an alternate embodiment of the present surgical tool holder 10 is shown. In this embodiment, the tool holder 10 has a safety release 350 having a safety release pin 351 connected to a base plate 352. Also connected to the base plate is a second spring pin 353, which is spaced apart and parallel with the release pin 351. The second spring pin 353 has a boss 355, which retains a safety release spring 357. The release spring 357 acts between the boss 355 and a release spring seat surface 359 of the housing 16c to hold the safety release in a normally closed condition by biasing the release pin 351 upward in a position which holds the cross pin 246 of the drive train 50c against the catch 244. Preferably, the release pin 351 has a rounded head 361 to facilitate removal of a pivot pin 246 from its respective catch 244 and allowing disassembly of the tool holder 10 for cleaning/sterilization. Further, the overall normal bias force of the safety release 350 is selected so as to release the pivot pins 246 from their respective catches 244 when the torsion or the stress on the drive train 50c (for example, from use of the holder 10 as an impactor) reaches a certain amount that, if exceeded, might damage the drive train 50c. Typically, such stresses occur when there is no tension on the drive train 50c and the pivot pins 246 collide with the safety release pin 351. Using this embodiment, it is also possible to release the pivot pin 246 from the catch 244 by the operator pulling down on a portion of the plate 352 that extends beyond the housing 16c.

Figure 12:
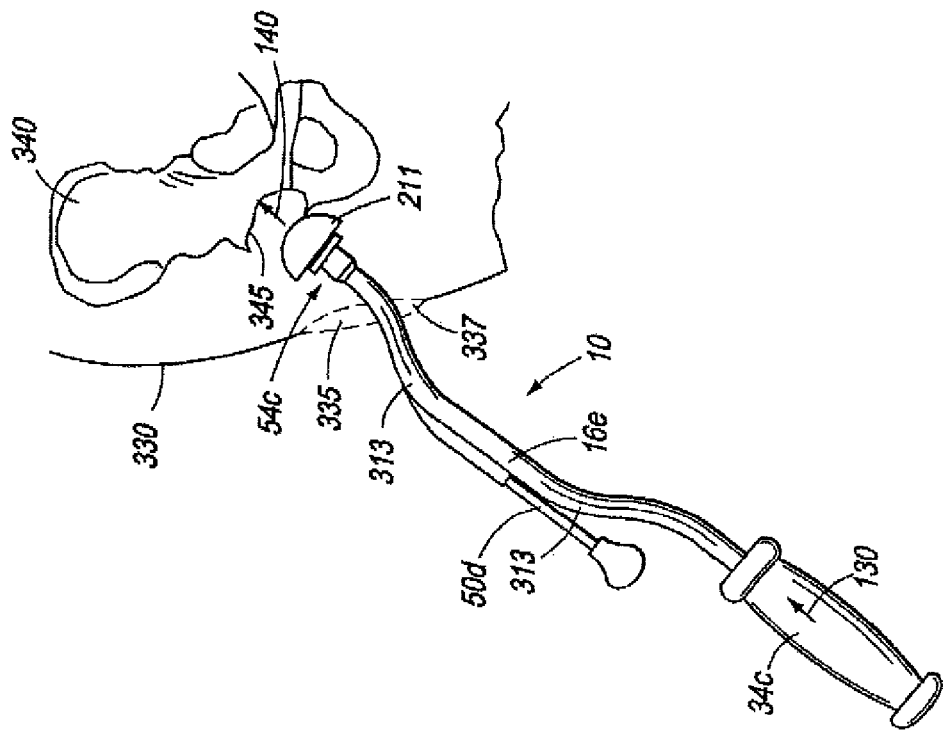
FIG. 12 is a schematic view of the surgical tool holder of the invention in operation.
Figure 11:
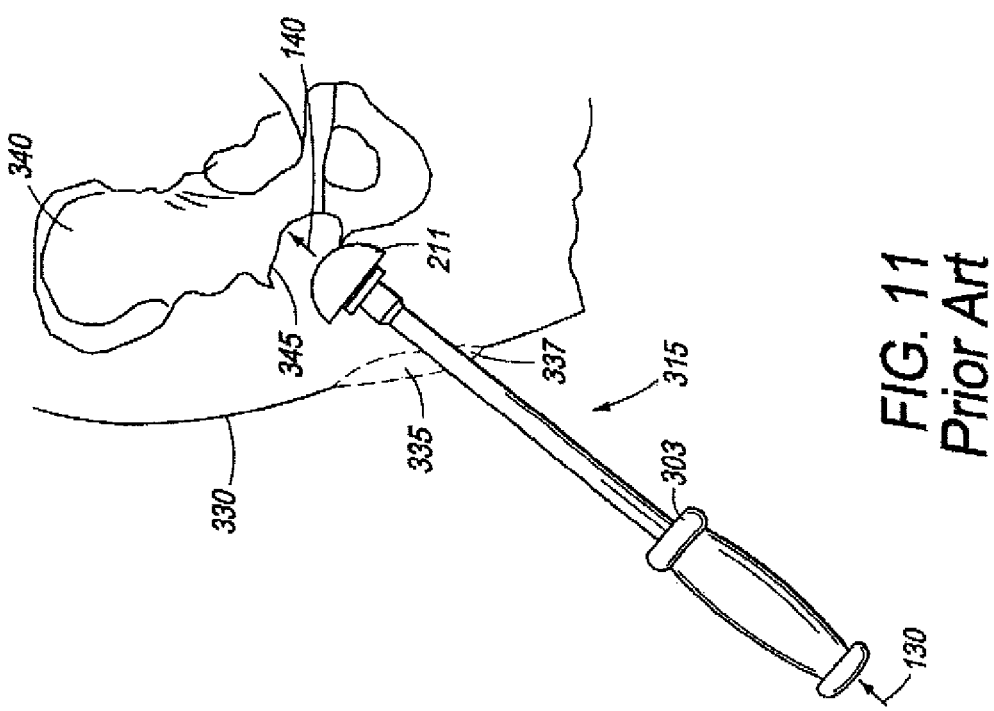
FIG. 11 is a schematic view of a prior art tool holder.

FIGS. 11 and 12 represent a prior art holder 315 and the present surgical tool holder 10 respectively, passing through an incision 335 in a patient's skin 330. FIG. 12 shows the preferred embodiment of the present tool holder 10 which has an appropriately curved housing 16e containing the drive chain 50d. The figures illustrate the benefit of a "C"-shaped housing 16e, in that in FIG. 12 the tool holder 10 is shown approaching the acetabulum 340 in an orientation desirable to ream the socket 345. A difficulty with the prior art "spindle"-type tool holder 315 in FIG. 11 is shown as the shaft 303 impinging on the miniature incision 335 at edge of the incision 337. Current surgical protocols are being pushed to the limits, with incision sizes being reduced to increase the patient's recovery speed. In some cases, surgeons are using a two-incision approach, one to reach the acetabulum and the other to reach the femur. Both the one incision and the two-incision technique demand less trauma to the patient, requiring the instruments to be more optimally designed to make up for the lack of operating space.

It is important to place the bends or off-sets 313 in the housing 16e at critical locations to pass through a miniature incision 335 without impinging on the skin at the edge 337 of the incision, while still maintaining the miniature incision surgical protocol. The bends/off-sets 313 are further disposed so that the grip end 34c of the holder 10 and the tool holder end 54c of the drive chain 50c have parallel axes, so that an applied force 130 on the grip end 34c results in an axial motion 140 at the tool holder end 54c. This configuration allows the operator to maintain the desired miniature incision technique using a curved housing embodiment of the present tool holder 10, without the above noted difficulty inherent in the use of the prior inserter 315 of FIG. 11. Additionally, in use, a curved housing embodiment of the present tool holder 10 provides the same benefit as a prior straight "spindle"-type tool holder of allowing the surgeon to apply a load directly along the path of reaming.

It is inherent in the present surgical tool holder 10 that alternative housing heads 264 can be mounted onto the front of the tool holder 10, which alternative heads 264 conform with a surface of specific alternative attachment 211, such as, an acetabular cup liner, in order to enable the device to seat a liner as well as the acetabular cup illustrated. In an advantage, the present tool handle 10 is simple and easy to use, without complex and possibly confusing locks. It is an object of the present invention is to minimize the risk that parts could be lost by having the holder 10 be partially disassemblable for cleaning and sterilization, but having all component parts remaining linked together.

Figure 13B:
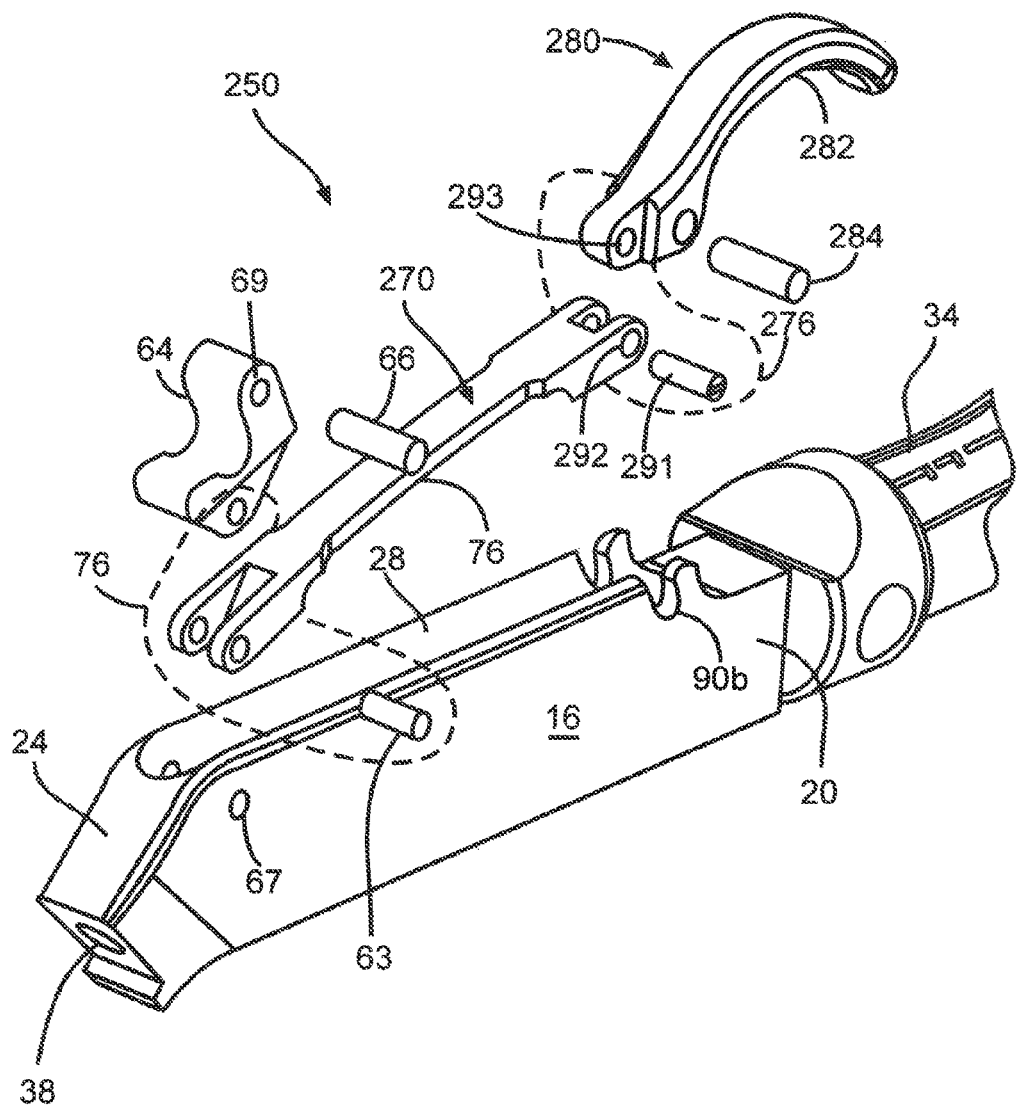
FIG. 13B is an exploded perspective view of the surgical tool holder of FIG. 6A.

Illustrated in FIGS. 13A and 13B, is a preferred embodiment of the holder 10, wherein the linkage assembly 250 has a rigid connecting rod 270, relative to the torsion connecting rod 70 of the preceding examples. As used herein, a rigid connecting rod refers to a connecting rod that has limited flexion capability. The embodiment of FIGS. 13A and 13B additionally has several unique features of the locking mechanism 100d, although a user generally operates the device 10 in a manner essentially as described above. Specifically, the locking mechanism 100d does not depend on the flexion of the connecting rod 270 (as in the embodiment of FIGS. 2A and 2B) to provide the bias force holding the linkage assembly 250 in a closed and locked configuration within the housing 16. In a preferred embodiment, the mechanical movement connector 76 at the drive end 72 (referred to previously as the "tool end") of the linkage assembly 250 can be substantially similar to the analogous mechanical connections of the embodiment of FIGS. 2A and 2B. However, the mechanical movement connector 76 at the driven end 74 of the linkage assembly 250 (referred to previously as the "grip end") is a "cam-pin" movement connector 276 (FIG. 14A), and is structurally and operationally different from the movement connector 76 at the drive end 72, while still accomplishing the function of a movement connector and an added functionality related to the locking mechanism 100d.

Figure 14A:
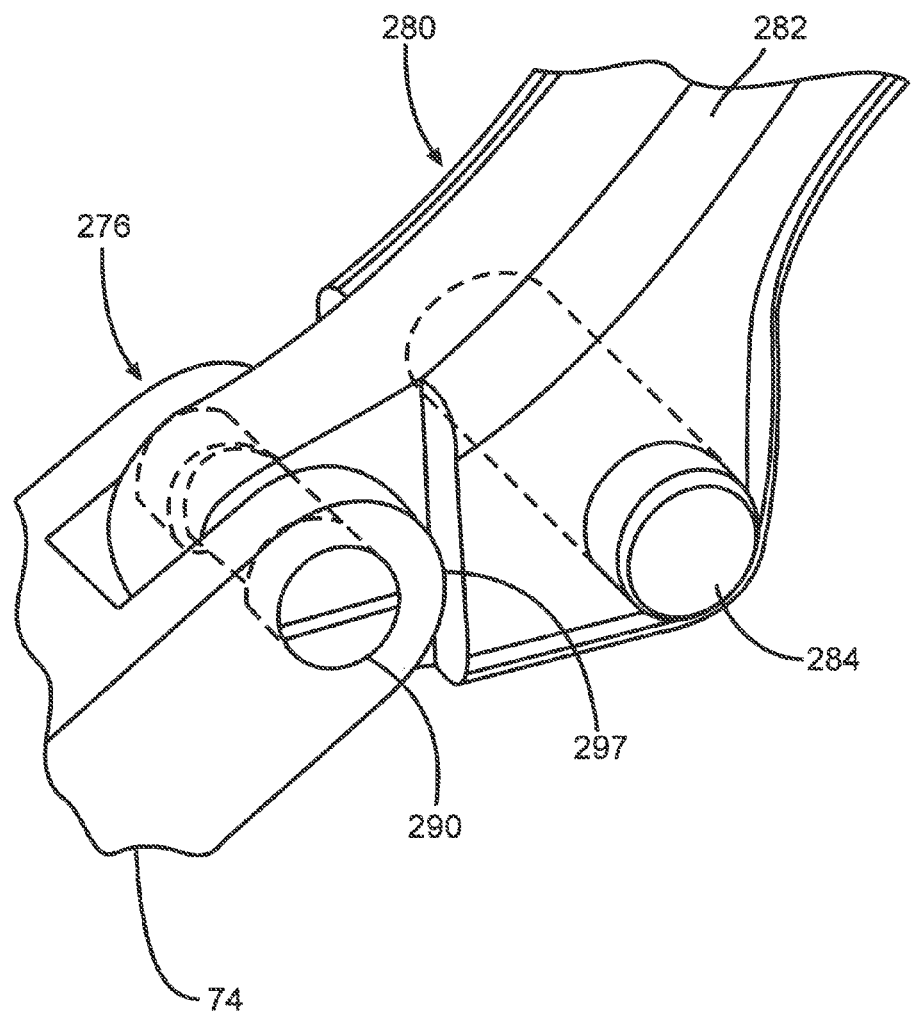
FIG. 14A is a close-up perspective view of the linkage assembly portion of the cam-pin engagement lever locking feature of FIGS. 6A and 6B.
Figure 14B:
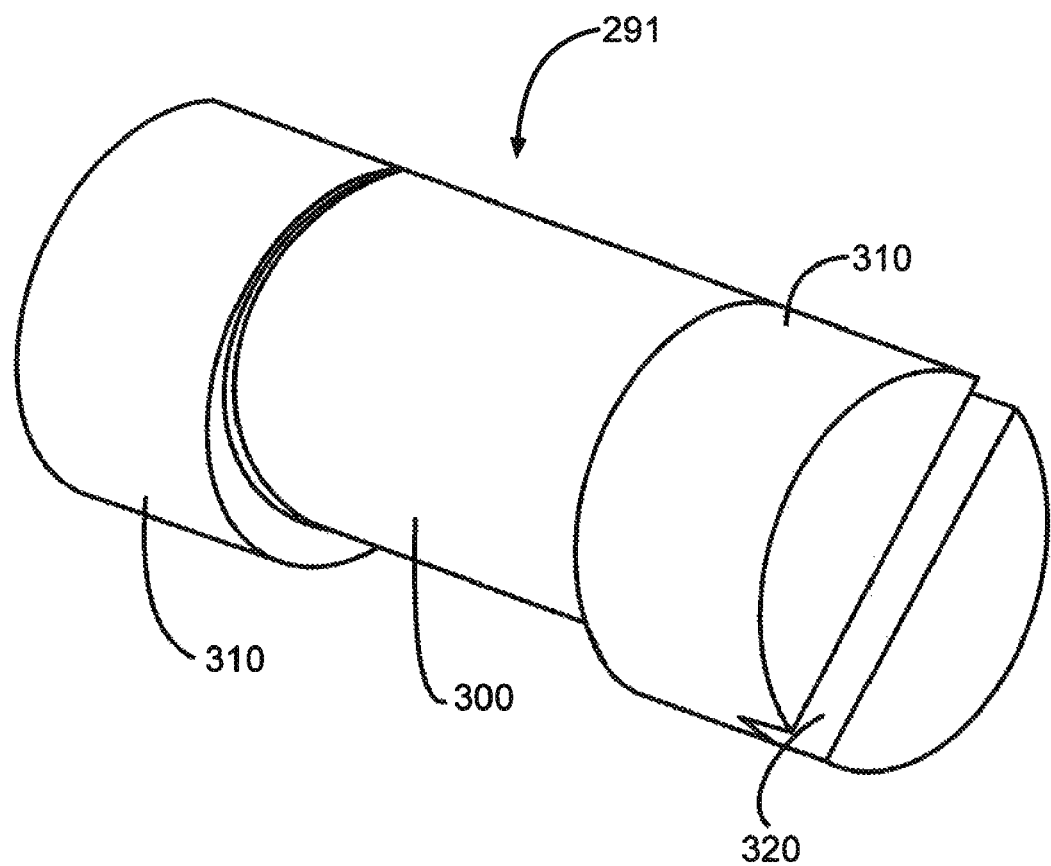
FIG. 14B is a close-up perspective view of the cam-pin of the cam-pin engagement lever locking feature disposed on the linkage assembly.

FIGS. 14A and 14B are close-up perspective views of the cam-pin movement connector 276 and the cam-pin 291, respectively, of the engagement lever locking mechanism 100d. The cam-pin 291 of the cam-pin movement connector 276 has an center section 300 providing a cam-shaped cross-section (e.g., has an eccentric cross-section relative to the cam-pin ends 310, in the embodiment illustrated). The center section 300 of the cam-pin 291 is closely but rotatably received in the cam-pin bore 293 (FIG. 13B) in the follower arm 282 of the engagement lever 280. The cam-pin ends 310 are received in the cam-pin mounts 292 (FIG. 13B) disposed on the driven end 74 of the connecting rod 270 in a relatively fixed and substantially non-rotating manner. In the embodiment illustrated, the cam-pin ends 310 are press/friction fitted into the cam-pin mounts 292. In a preferred embodiment one cam-pin end 310 of the cam-pin 291 has a hand tool interface 320 (a slot for receiving a screw driver in the illustrated embodiment). The tool interface 320 allows the cam-pin 291 to be forceably rotated against the friction of the cam-pin mounts 292 to adjust the relationship of the eccentric center section 300 of the cam-pin 291 relative to the axis 294 of the cam-pin mounts 292. In other words, the cam-pin 291 may be rotated such that its eccentric center section 300 is moved relative to the cam-pin mounts 292. The relative movement of the eccentric center section 300 is sufficient to move the rigid connecting rod 270 and, likewise, the locking paw 65, relative to the detent 42 in the tool head 40 (see FIGS. 2A and 2B).

The relationship of the eccentric center section 300 of the cam-pin 291 relative to the axis 294 of the cam-pin mounts 292 is set so that, when the lever pin 284 is seated in the catch recesses 90b (FIG. 13B), and the engagement lever 280 is down (as in FIG. 2B), or, more generally, the engagement lever 280 is in a position to engage the locking mechanism 100d with the tool (known herein as an engagement lever lock position), the eccentric center section 300 is disposed more toward the proximal face 297 (FIG. 14A) of the driven end 74 of the connecting rod 270. In this condition with the engagement lever 280 in the engagement lever lock position (as in FIG. 2B), the connecting rod 270 forces and holds the locking pawl 64 in engagement with the detent 42 in the tool head 40 to secure the tool 40 to the handle 10 (as in FIG. 2A). This configuration causes an "over-center" condition of the cam-pin 291 relative to the lever pin 284 due to the resistive force exerted by the connecting rod 270 (when the pawl 64 is driven against the tool detent 42) on the cam-pin 291, which acts to hold the locking mechanism 100d in the locked condition.

When the engagement lever 280 is raised, or, more generally, the engagement lever 280 is in a position to dis-engage the locking mechanism 100d from the tool (known herein as an engagement lever unlock position, as illustrated in FIG. 2A), the locking mechanism 100d is released. In this condition, the "over-center" condition is removed, and the linkage assembly 250 may be disengaged from a tool head and pivoted out of the housing for cleaning. FIG. 14B is a close-up perspective view of the cam-pin 291 showing the relationship of the eccentric center section 300 to the cam-pin ends 310.

The "over-center" condition of the cam-pin 291 relative to the lever pin 284 refers to a configuration having two stable positions of the locking mechanism 100d. When the engagement lever 280 is in the engagement lever lock position, the lever pin 284 is disposed in the catch recess 90b (FIG. 13A). The connecting rod 270 is pushed toward the tool end 76 of the linkage assembly 250, causing the pawl to engage with the detent 42 of the tool head 40. In this first stable position, the cam-pin 291 has a first position relative to the lever pin 284. In the second stable position, the cam-pin 291 has a second position relative to the lever pin 284.

When the engagement lever 280 is in the engagement lever unlock position, the lever pin 284 is no longer positioned in the catch recess 90b. The rigid connecting rod 270 is pulled back from the tool end, and the tool head 40 is released from the locking pawl 65. In this second stable position, the cam-pin 291 has a second position relative to the lever pin 284, the second position being different from the first position. In other words, the mechanism toggles over center from one stable position to another stable position which, in this case, enables disassembly of the mechanism.

Figure 15:
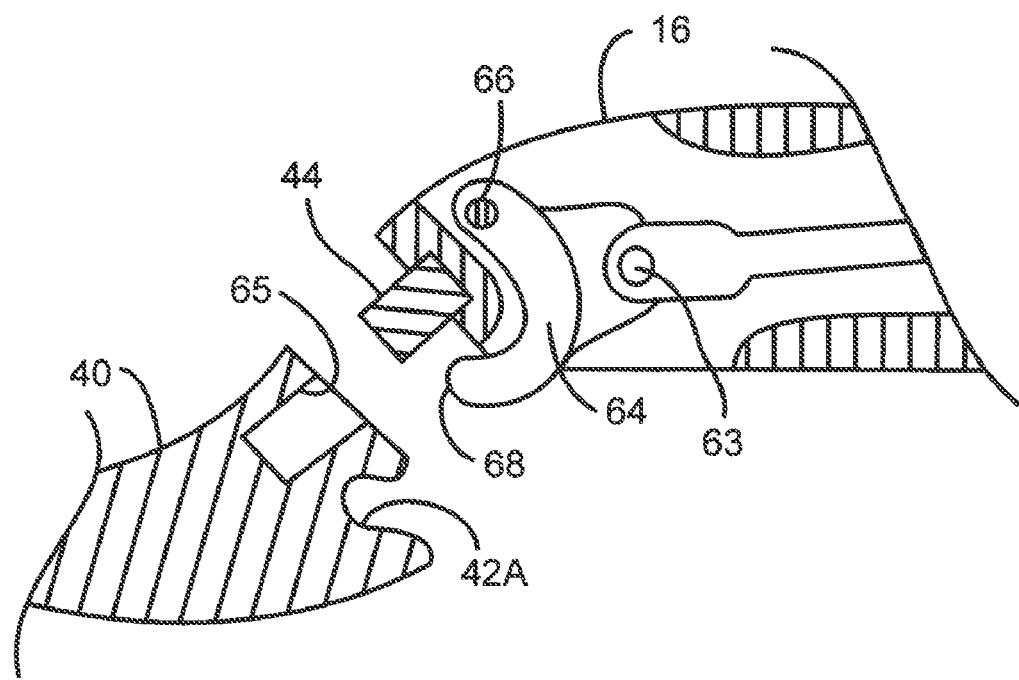
FIG. 15 is a cross-sectional side view of an alternative embodiment of a tool interface.

FIG. 15 is a cross-sectional side view of an alternative embodiment of a tool interface 38a for practice in the present tool holder 10. In this embodiment, the key 44 is disposed on the tool end 24 of the housing 16, instead of on the tool head 40a, as in FIGS. 2A and 2B. Further, the detent 42a is located on the tool head 40a in a different manner than in FIGS. 2A and 2B. However, forward movement of the pawl 65 still causes the locking face 68 to engage a detent 42a in the tool head 40a to secure the tool 40a to the handle 10.

The surgical tool holders described above may be connected to a variety of tools, including, but not limited to, broaches, rasps, reamers, angled drivers, twist drills, flexible drills, cannulated drills, bayonet drills, bayonet taps, drill guides, adjustable angle drill guides, taps, and cannulated taps.

Multiple variations and modifications are possible in the embodiments of the invention described here. Although certain illustrative embodiments of the invention have been shown and described here, a wide range of modifications, changes, and substitutions is contemplated in the foregoing disclosure. In some instances, some features of the present invention may be employed without a corresponding use of the other features. Accordingly, it is appropriate that the foregoing description be construed broadly and understood as being given by way of illustration and example only, the spirit and scope of the invention being limited only by the appended claims.

What is claimed is:

1. A surgical tool holder comprising:
   a) a housing providing a linkage chamber extending from a proximal housing grip end to a distal housing tool end for receiving a tool;
   b) a tool holder linkage at least partially disposed within the linkage chamber, the tool holder linkage comprising:
      i) an engagement lever attached to the housing by a proximal pivot pin to thereby provide a first pivotable connection between the engagement lever and the housing at the proximal pivot pin;
      ii) a locking pawl attached to the housing by a distal pivot pin to thereby provide a second pivotable connection between the locking pawl and the housing at the distal pivot pin; and
      iii) a connecting rod comprising a proximal connecting rod end connected by a cam-pin to the engagement lever adjacent to the proximal housing end in a third pivotable connection and a distal connecting rod end connected by a pawl pin to the locking pawl adjacent to the distal housing end in a fourth pivotable connection; and
   c) wherein the engagement lever is manipulatable from a first, opened position spaced a maximum distance along a range of motion from the proximal housing end to a second, closed position spaced at a closer distance along the range of motion relative to the proximal housing end than the first position to thereby cause the connecting rod to move in a distal direction with the distal connecting rod end at the fourth pivotable connection with the locking pawl causing the pawl to pivot with respect to the housing at the second pivotable connection on the distal pivot pin from an open configuration ready to receive a tool for attachment to the housing to a closed configuration engageable with a tool supported at the distal housing tool end.

2. The surgical tool holder of claim 1, wherein the proximal pivot pin comprises a pair of opposed proximal lever pins centered on an engagement lever axis with the housing including a pair of catch recesses proximate the proximal housing grip end, each catch recess disposed to pivotably receive one of the pair of proximal lever pins to mount the engagement lever to the housing.

3. The surgical tool holder of claim 1, wherein the cam pin is rotatable to adjust a relationship between an eccentric center section axis and a cam-pin mounts axis.

4. The surgical tool holder of claim 3, the cam-pin comprising a hand tool interface for rotatably adjusting the relationship between the eccentric center section axis and the cam-pin mounts axis.

5. The surgical tool holder of claim 4, wherein the proximal pivot pin is engaged into a catch recess of the housing when the engagement lever is moved to the second closed position.

6. The surgical tool holder of claim 1 wherein with the engagement lever in the first, opened position, the third pivotable connection between the proximal connecting rod end and the engagement lever at the cam-pin is neither more proximal nor more distal than the first pivotable connection of the engagement lever and the housing at the proximal pivot pin.

7. The surgical tool holder of claim 1 wherein with the engagement lever in the second, closed position, the third pivotable connection between the proximal connecting rod end and the engagement lever at the cam-pin is more distal than the first pivotable connection of the engagement lever and the housing at the proximal pivot pin.

8. The surgical tool holder of claim 1 wherein with the engagement lever in the first, opened position, the fourth pivotable connection between the distal connecting rod end and the locking pawl at the pawl pin is more proximal than the second pivotable connection of the locking pawl and the housing at the distal pivot pin.

9. The surgical tool holder of claim 1 wherein with the engagement lever in the second, closed position, the fourth pivotable connection between the distal connecting rod end and the locking pawl at the pawl pin is more distal than the second pivotable connection of the locking pawl and the housing at the distal pivot pin.

10. The surgical tool holder of claim 1 wherein the proximal pivot pin pivotally supports the tool holder linkage for pivotable movement out of the linkage chamber for cleaning with the tool holder linkage remaining connected to the housing at the second pivotable connection with the distal pivot pin.

11. The surgical tool holder of claim 1 wherein the tool holder linkage is removably attached to the housing at the proximal pivot pin by a linkage lock mechanism such that when the linkage lock mechanism is released, the tool holder linkage is pivotable out of the linkage chamber for cleaning with the tool holder linkage remaining connected to the housing at the second pivotable connection with the distal pivot pin.

12. The surgical tool holder of claim 11 wherein the linkage lock mechanism comprises a detent bias that bears against the proximal pivot pin.

13. The surgical tool holder of claim 12 wherein the detent bias is either integral or not integral with the housing.

14. The surgical tool holder of claim 1 wherein a hand grip is attached to the housing at the proximal housing grip end.

15. The surgical tool holder of claim 1 wherein an obstruction mounted on the housing is manipulatable from a locked position preventing the engagement lever from being inadvertently moved out of the second, closed position to a retracted position which allows for free movement of the engagement lever between the first and second positions.

16. A kit, comprising:
   a) a container;
   b) a surgical tool holder according to claim 1, wherein the surgical tool holder is disposed within the container; and
   c) a tool to be connected to the surgical tool holder, wherein the tool is selected from a group consisting of broaches, rasps, reamers, angled drivers, twist drills, flexible drills, cannulated drills, bayonet drills, bayonet taps, drill guides, adjustable angle drill guides, taps, and cannulated taps.

17. The kit of claim 16 comprising instructions for connecting the tool to the surgical tool holder.

18. A surgical tool holder comprising:
   a) a housing comprising opposed housing sidewalls providing a linkage chamber therebetween, the housing sidewalls extending from a proximal housing grip end to a distal housing tool end for receiving a tool;

b) a tool holder linkage at least partially disposed within the linkage chamber, the tool holder linkage comprising:
  i) an engagement lever attached to the housing by a proximal pivot pin having opposed ends pivotally supported by the opposed housing sidewalls to thereby provide a first pivotable connection between the engagement lever and the housing at the proximal pivot pin;
  ii) a locking pawl attached to the housing by a distal pivot pin having opposed ends pivotally supported by the opposed housing sidewalls to thereby provide a second pivotable connection between the locking pawl and the housing at the distal pivot pin; and
  iii) a connecting rod at least partially disposed within the linkage chamber, the connecting rod comprising a proximal connecting rod end connected by a cam-pin to the engagement lever adjacent to the proximal housing end in a third pivotable connection and a distal connecting rod end connected by a pawl pin to the locking pawl adjacent to the distal housing end in a fourth pivotable connection; and
c) wherein the engagement lever is manipulatable from a first, opened position spaced a maximum distance along a range of motion from the proximal housing end to a second, closed position spaced at a closer distance along the range of motion relative to the proximal housing end than the first position to thereby cause the connecting rod to move in a distal direction with the distal connecting rod end at the fourth pivotable connection with the locking pawl causing the pawl to pivot with respect to the housing at the second pivotable connection on the distal pivot pin from an open configuration ready to receive a tool for attachment to the housing to a closed configuration engageable with a tool supported at the distal housing tool end; and
d) wherein with the engagement lever in the first, opened position, the fourth pivotable connection between the distal connecting rod end and the locking pawl at the pawl pin is more proximal than the second pivotable connection of the locking pawl and the housing at the distal pivot pin and with the engagement lever in the second, closed position, the fourth pivotable connection between the distal connecting rod end and the locking pawl at the pawl pin is more distal than the second pivotable connection of the locking pawl and the housing at the distal pivot pin.

19. The surgical tool holder of claim 18 wherein the tool holder linkage is removably attached to the housing at the proximal pivot pin by a linkage lock mechanism such that when the linkage lock mechanism is released, the tool holder linkage is pivotable out of the linkage chamber for cleaning with the tool holder linkage remaining connected to the housing at the second pivotable connection with the distal pivot pin.

20. A surgical tool holder comprising:
a) a housing comprising opposed housing sidewalls providing a linkage chamber therebetween, the housing sidewalls extending from a proximal housing grip end to a distal housing tool end for receiving a tool;
b) a tool holder linkage at least partially disposed within the linkage chamber, the tool holder linkage comprising:
  i) an engagement lever attached to the housing by a proximal pivot pin having opposed ends pivotally supported by the opposed housing sidewalls to thereby provide a first pivotable connection between the engagement lever and the housing at the proximal pivot pin;
  ii) a locking pawl attached to the housing by a distal pivot pin having opposed ends pivotally supported by the opposed housing sidewalls to thereby provide a second pivotable connection between the locking pawl and the housing at the distal pivot pin; and
  iii) a connecting rod at least partially disposed within the linkage chamber, the connecting rod comprising a proximal connecting rod end connected by a cam-pin to the engagement lever adjacent to the proximal housing end in a third pivotable connection and a distal connecting rod end connected by a pawl pin to the locking pawl adjacent to the distal housing end in a fourth pivotable connection; and
c) wherein the engagement lever is manipulatable from a first, opened position spaced a maximum distance along a range of motion from the proximal housing end to a second, closed position spaced at a closer distance along the range of motion relative to the proximal housing end than the first position to thereby cause the connecting rod to move in a distal direction with the distal connecting rod end at the fourth pivotable connection with the locking pawl causing the pawl to pivot with respect to the housing at the second pivotable connection on the distal pivot pin from an open configuration ready to receive a tool for attachment to the housing to a closed configuration engageable with a tool supported at the distal housing tool end; and
d) wherein the proximal pivot pin pivotally supports the tool holder linkage for pivotable movement out of the linkage chamber for cleaning with the tool holder linkage remaining connected to the housing at the second pivotable connection with the distal pivot pin.

21. The surgical tool holder of claim 20 wherein with the engagement lever in the first, opened position, the third pivotable connection between the proximal connecting rod end and the engagement lever at the cam-pin is neither more proximal nor more distal than the first pivotable connection of the engagement lever and the housing at the proximal pivot pin.

22. The surgical tool holder of claim 20 wherein with the engagement lever in the second, closed position, the third pivotable connection between the proximal connecting rod end and the engagement lever at the cam-pin is more distal than the first pivotable connection of the engagement lever and the housing at the proximal pivot pin.

23. The surgical tool holder of claim 20 wherein with the engagement lever in the first, opened position, the fourth pivotable connection between the distal connecting rod end and the locking pawl at the pawl pin is more proximal than the second pivotable connection of the locking pawl and the housing at the distal pivot pin.

24. The surgical tool holder of claim 20 wherein with the engagement lever in the second, closed position, the fourth pivotable connection between the distal connecting rod end and the locking pawl at the pawl pin is more distal than the second pivotable connection of the locking pawl and the housing at the distal pivot pin.

* * * * *